Aug. 8, 1972 H. MOTZKAU Plant Pat. 3,251
AZALEA PLANT
Filed Dec. 29, 1970
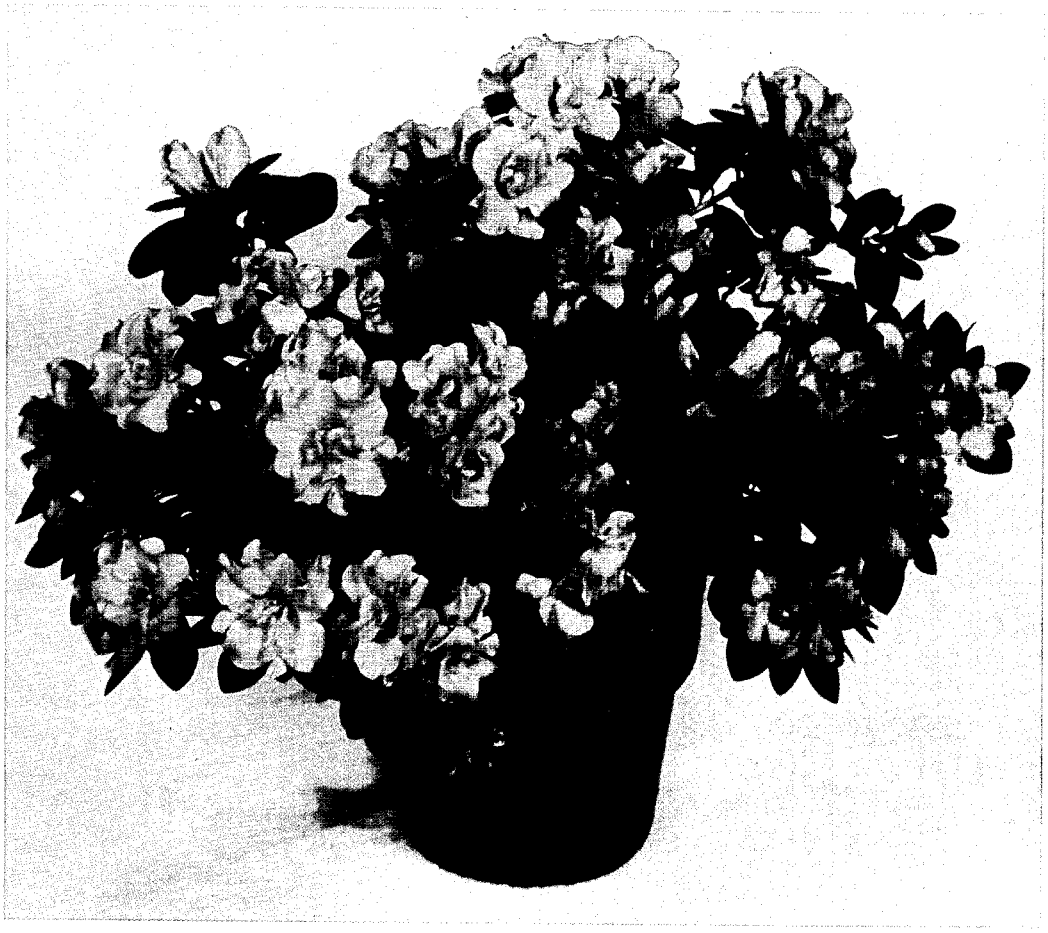

United States Patent Office

Plant Pat. 3,251

Patented Aug. 8, 1972

3,251
AZALEA PLANT

Henry Motzkau, Whitewater, Wis., assignor to Yoder Brothers, Inc., Barberton, Ohio

Filed Dec. 29, 1970, Ser. No. 102,565
Int. Cl. A01h *5/00*
U.S. Cl. Plt.—57 1 Claim

The present invention comprises a new and distinct cultivar of azalea plant which has resulted from crossing certain azalea selections in a program of controlled hybridization. The seed parent is identified for breeding purposes by #1223, and the pollen parent by #969. Both of these parents are unpatented and identified in this manner to distinguish the same from other parents in the same breeding program.

ing environmental conditions such as temperature, day length and light intensity. Suggested flowering period is from mid-December through March in a natural season program and January through December in a year round controlled program.

The accompanying drawing shows the unique features of the new cultivar, the colors being as nearly true as possible with color illustrations of this type.

In the description which follows, color references are to the Munsell Color Book, 1963 edition, and color comparisons have been made with the cultivar Valentine.

Botanical classification: *Rhododendron hybrida* evergreen type.

Flower: Spring color.

Color: (May in Barberton, Ohio).

| | Redhawk | Valentine |
|---|---|---|
| General tonality | Rose red, 10RP4/12 | Vivid red, 5R5/13 to 5R5/14. |
| Sepals first divide | Dark rose red, 10RP4/10 | Vivid red, 5R5/13. |
| Petals unfurl | Dark rose red, 2.5R3/10 | Vivid red, darker than 5R5/13. |
| Fully open: | | |
| Inside | Rose red, 10RP4/12 | Vivid red, 5R5/13. |
| Reverse | Rose red, lighter than 10RP4/12 | Less luminous than 5R5/13. |
| Base of petals | Scarlet red near 6.25R4/14 | |
| Outer hose | Darker rose red, 10RP4/14 | |
| Discloration as ages | Gradual oxidation becomes purplish-red, 7.5RP2/6 when dry. | |

The new cultivar is similar in many respects to Valentine, U.S. Plant Pat. No. 2,492, having the same characteristics as Valentine of:

(1) Rapid growth.
(2) Semi-upright compact growth habit.
(3) Semi-double hose in hose flower form.

The new cultivar is distinguished from Valentine by the following characteristics:

(1) Its ability to be flowered all 12 months in a controlled flowering program. Valentine is recommended particularly from October through mid-March.

(2) Its early-mid-season natural flowering response vs. Valentine mid-season response.

(3) It does not revegetate as readily or develop as many lateral suckers around the flower bud during forcing.

(4) It buds more readily and uniformly.

(5) It forces more readily and uniformly.

(6) Its excellent keeping quality.

(7) Its dark rose red color.

(8) It develops a finished plant 15–20% larger in diameter from liners of equal size.

The new cultivar was selected from a progency of seedlings from the above-mentioned parents. Varietal worth was determined by flowering liners from cuttings taken from the initial selection in both a year round and natural season developmental flowering program over a period of 5 years in Ohio. Stock growth was evaluated in southern Florida.

The new cultivar has been asexually reproduced by cuttings at Whitewater, Wis., and has been found to retain its distinctive characteristics through successive propagations.

The new cultivar when grown in the vicinity of Barberton, Ohio, has a response described as early-mid-season and the following detailed description is based on observations made of the new cultivar in a greenhouse in Barberton, Ohio. The response time, blooming period, color, and total vigor may vary significantly with vary-

*Bud.*—Size—medium; form—conoidal; opening habit—open cup-like. Retains cup-like form.

*Bloom.*—Size—medium; average—2"; range—1¾"–2¾"; borne—several together; average—3; range 1–4; form—hose on hose semi-double with petaloids to varying degrees.

*Blooming habit.*—Once; profusely; response—natural season—early, mid-season, mid-December through March; year round—early, mid-season, all 12 months. Sepals—"Bud Sheath"—normal, smooth edge, hairy, drops as buds open. Peduncle—length—short; aspect—hairy; strength—strong.

*Petals.*—Texture—soft; appearance—inside, satiny; outside, satiny; form—rounded and somewhat notched; arrangement—imbricate with petaloids; fragrance—none; persistence—hang on and dry; non-shatter; longevity—(keeping quality) greenhouse—2½ weeks+; home—3 weeks+.

*Reproductive organs.*—Stamen—5–10, many of them petaloid; anthers—color, dark red, 7.5R2/2, normal; filaments—thin, if present, red, 5R4/14; style—columnar, medium-long; may be fasciated, red 5R4/14; stigma—may be fasciated, red, 5R3/12; ovaries—hypogynous; fruit—none.

Plant:

*Bush form.*—Growth habit—compact; semi-upright; breaking habit—vigorous, semi-upright, size—average finished product from No. 7 liner—height, 10"–12"; diameter, 11"–14"; rooting habit—good, easy, from own roots; budding ease—good under wide range of conditions; uniformity of budding—good; growth regulator—not needed.

*Foliage.*—Type—evergreen; leaflets—single; size—length—average—2"; range—1½"–2½"; width—average—1"; range—¾"–1⅜"; shape—ovate to obovate; texture—upper—glossy; lower—glossy; rib and mid-veins—slightly depressed; edge—smooth.

| Color | Redhawk | Valentine |
|---|---|---|
| New foliage: | | |
| Upper | Light green, 5GY4/6 | Ligh green, 7.5GY6/8 to 7.5GY5/7. |
| Lower | Light Yellow green, 5GY5/4 | Light green, 10GY6/9 to 10GY5/8. |
| Mature foliage: | | |
| Upper | Green, 7.5GY3/4 | |
| Lower | Gray green, 7.5GY5/4 | |

Petiole—medium green, 5GY6/6.

| Color | Redhawk | Valentine |
|---|---|---|
| Stems: | | |
| New wood | Green, 5GY7/4 | Light green, 7.5GY6/9. |
| Mature wood | Yellow brown, 10YR3/6 | |

*Responsiveness to day length and temperature.*—Buds and flowers under wide range of conditions.

*Resistance to Cylindrocladium.*—Good.

*Cooler tolerance.*—Good.

*Shipping tolerance.*—Good.

I claim:

1. A new and distinct cultivar of Azalea characterized particularly as to novelty when compared with the cultivar Valentine by its ability to be flowered all 12 months in a controlled flowering program, its excellent keeping qualities, its dark rose red color, its early-mid-season response, its ability to bud uniformly under a wide range of environmental conditions, its 15–20% larger diameter as a finished plant from liners of equal size, and its ability under usual conditions of not revegetating during the forcing period.

No references cited.

ROBERT E. BAGWILL, Primary Examiner